United States Patent [19]

Tuloup et al.

[11] Patent Number: 5,132,106
[45] Date of Patent: * Jul. 21, 1992

[54] HALOGENATED PYRIMIDINE 3-OXIDE DERIVATIVES, THEIR USE FOR THE TREATMENT AND PREVENTION OF HAIR LOSS AND FOR STIMULATING ITS REGROWTH

[75] Inventors: Remy Tuloup, Miniac-sous-Becherel; Alex Junino, Livry-Garoan; Michel Hocquaux, Paris; Jacqueline Dumats, Villepinte; Quintino Gaetani, Sevran, all of France

[73] Assignee: L'oreal, Paris, France

[*] Notice: The portion of the term of this patent subsequent to Nov. 27, 2007 has been disclaimed.

[21] Appl. No.: 551,534

[22] Filed: Jul. 12, 1990

Related U.S. Application Data

[63] Continuation-in-part of Ser. No. 387,590, Jul. 31, 1989, Pat. No. 4,973,474.

[30] Foreign Application Priority Data

Jul. 12, 1989 [EP] European Pat. Off. ........ 89402002.3
Jan. 31, 1990 [FR] France ................. 90 01148

[51] Int. Cl.⁵ .................... A61K 7/06; A61K 31/505
[52] U.S. Cl. ....................... 424/70; 514/272
[58] Field of Search ................... 424/70; 514/272

[56] References Cited

U.S. PATENT DOCUMENTS 4,973,474 11/1990 Hocquaux et al. .................. 424/70

FOREIGN PATENT DOCUMENTS

WO86/00616 1/1986 PCT Int'l Appl. .

*Primary Examiner*—Frederick E. Waddell
*Assistant Examiner*—Diane Gardner
*Attorney, Agent, or Firm*—Fleit, Jacobson, Cohn, Price, Holman & Stern

[57] ABSTRACT

The invention relates to compounds of formula:

$$R_2HN-\text{[pyrimidine 3-oxide]}-NHR_1 \quad (I)$$

in which:

$R_1$ and $R_2$ denote, independently of one another, a hydrogen atom or alternatively a carbamoyl group of formula:

$$-\underset{\underset{O}{\parallel}}{C}-N\underset{R'_3}{\overset{R_3}{\diagup}} \quad (B)$$

with $R'_3$ denoting hydrogen or $R_3$; an alkoxycarbonyl group of formula:

$$-\underset{\underset{O}{\parallel}}{C}-OR_3 \quad (C)$$

or an acyl group of formula:

$$-\underset{\underset{O}{\parallel}}{C}-R_3 \quad (D)$$

in which formulae $R_3$ denotes an alkyl, alkenyl or cycloalkyl radical; $R_3$ can also denote an aryl or aralkyl radical; and R denotes a linear or braanched $C_1$-$C_8$ alkyl radical substituted with one or more halogen atoms, and to their use for the treatment and prevention of hair loss and for stimulating its regrowth.

14 Claims, No Drawings

HALOGENATED PYRIMIDINE 3-OXIDE DERIVATIVES, THEIR USE FOR THE TREATMENT AND PREVENTION OF HAIR LOSS AND FOR STIMULATING ITS REGROWTH

This application is a continuation-in-part of U.S. application Ser. No. 07/387,590, filed Jul. 31, 1989, now U.S. Pat. No. 4,973,474.

The present invention relates to new halogenated pyrimidine 3-oxide derivatives, and to the preparation of cosmetic or pharmaceutical compositions intended, in particular, for use in topical application in the treatment and prevention of hair loss and for stimulating its regrowth.

6-Piperidino-2,4-diaminopyrimidine 3-oxide or "minoxidil" is already known in the prior art for its use in the treatment of hair loss, pelade, desquamating dermatitis, alopecia, and the like.

The Applicant has just discovered new products derived from pyrimidine 3-oxide, substituted at the 6-position with a haloalkoxy group.

He discovered that these products when particularly effective for the treatment of hair regrowth, and especially for inducing and stimulating hair growth and checking its loss, and they could be, in particular, used in the treatment of diseases of the scalp such as pelade, desquamating dermatitis or alopecia.

Another advantage of these compounds is their exceptional solubility in media used for topical application.

The subject of the invention is hence new pyrimidine 3-oxide derivatives substituted at the 6-position with a haloalkoxy group.

Another subject of the invention consists of a process for preparing these.

The invention also relates to cosmetic and/or pharmaceutical compositions enabling these compounds to be used.

Other subjects of the invention will become apparent on reading the description and the examples which follow.

The compounds according to the invention are essentially characterized in that they correspond to the formula:

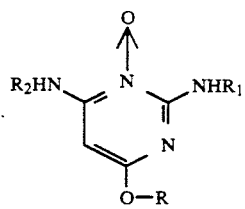
(I)

in which:

$R_1$ and $R_2$ denote, independently of one another, a hydrogen atom, a carbamoyl group of formula:

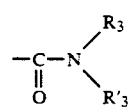
(B)

with $R'_3$ denoting hydrogen or $R_3$; an alkoxycarbonyl group of formula:

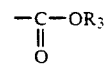
(C)

or an acyl group of formula:

(D)

in which formulae $R_3$ denotes a linear or branched $C_1$–$C_{18}$ alkyl radical, a $C_2$–$C_{18}$ alkenyl group or a $C_5$–$C_8$ cycloalkyl group; $R_3$ can also denote an aryl or aralkyl radical corresponding to the formula:

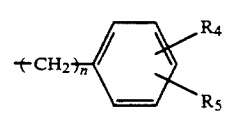
(E)

in which:

n is an integer which can vary between 0 and 4;

$R_4$ and/or $R_5$, independently of one another denote hydrogen, a $C_1$–$C_6$ lower alkyl group or a hydroxyl or $C_1$–$C_5$ alkoxy group; and as well as their addition salts with cosmetically or pharmaceutically acceptable acids.

Especially preferred compounds are those in which the halogen atoms denote fluorine or chlorine; in $C_1$–$C_6$ alkyl group represented by R denotes, in particular, a mono- or polyhalomethyl, -ethyl, or -propyl group; and $R_1$ and $R_2$ preferably denote hydrogen.

More especially preferred groups R are selected from —$CH_2CF_3$ and —$CH_2$—$CF_2$—$CHF_2$ groups.

More especially preferred compounds of the invention consist of 2,4-diamino-6-(2-trifluoroethyloxy)-pyrimidine 3-oxide and 2,4-diamino-6-(2,2,3,3-tetrafluoropropyloxy)pyrimidine 3-oxide.

The compounds according to the invention can also exist in the tautomeric form, corresponding to the following formulae (IA) and (IB):

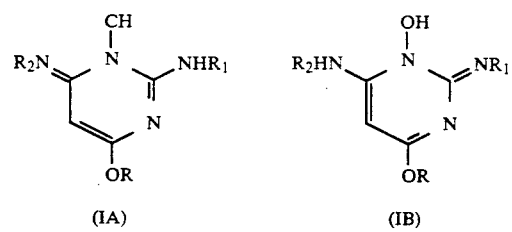

(IA)             (IB)

These tautomeric forms (I), (IA) and (IB) may be present in variable proportions, and one can be preponderant relative to the others.

The compounds according to the invention for which $R_1$ and $R_2$ denote hydrogen are prepared from 2,4-diamino-6-(2,4-dichlorophenoxy)pyrimidine 3-oxide or 2,4-diamino-6-chloropyrimidine 3-oxide, which is reacted with an alcoholate of formula $RO^\ominus Y^\oplus$, where R has the meaning stated above and Y is an alkali metal cation such as sodium, potassium or lithium.

The compounds for which $R_1$ and $R_2$ are carbamoyl, alkoxycarbonyl or acyl groups are obtained from the corresponding 2,4-diamino-6-haloalkoxypyrimidine 3-oxide derivatives whose preparation is described below.

The production of derivatives for which $R_1$ and $R_2$ are carbamoyl groups is generally carried out by reacting a carbamoyl chloride with the corresponding 2,4-diamino-6-haloalkoxypyrimidine 3-oxide derivatives in a polar solvent such a dimethyl sulphoxide, at a temperature of between 0° and 100° C., and more especially between 20° and 70° C.

The production of derivatives for which $R_1$ and $R_2$ are alkoxycarbonyl groups is generally carried out by the action of an excess of chloroformic ester on the corresponding 2,4-diamino-6-haloalkoxypyrimidine 3-oxide derivative, working in an aprotic polar solvent such as dichloromethane, in the presence of a teritary amine such as triethylamine or pyridine, at a temperature of between 0° and 50° C.

The production of derivatives for which $R_1$ and $R_2$ are acyl groups is generally carried out by reacting an acid chloride or an anhydride with the corresponding 2,4-diamino-6-haloalkoxypyrimidine 3-oxide derivative in an aprotic polar solvent such as dichloromethane, in the presence of a teritary amine such a triethylamine or pyridine, at a temperature of between 0° and 50° C.

From the compounds of formula (I), it is possible to prepare their addition salts with cosmetically or pharmaceutically acceptable acids, such as the salts with sulphuric, hydrochloric, hydrobromic, phosphoric, acetic, benzoic, salicylic, glycolic, succinic, nicotinic, tartaric, maleic, pamoic, methanesulphonic, picric and lactic acids, and the like.

The compounds according to the invention may be used in the cosmetic or pharmaceutical field, in particular in topical applications, and more especially in the treatment or prevention of hair loss, and more especially of pelade, alopecia and also desquamating dermatitis.

These compositions are essentially characterized in that they contain at least one compound corresponding to the formula (I) or one of its salts in a physiologically acceptable medium suitable for topical application.

These compositions can contain, by way of a physiologically acceptable medium, any medium suitable for topical application, ether in cosmetics or in pharmacy, and which is compatible with the active substance.

The compounds according to the invention can be present in this medium either in the dissolved state or in the dispersed state, in particular in micronized form.

The compositions intended for use in pharmacy are presented in the form of an ointment, tincture, cream, pomade, powder, patch, impregnated pad, solution, emulsion or vesicular emulsion, lotion, gel, spray or suspension. They can be either anhydrous or aqueous, depending on the clinical indication.

The compounds are present in these pharmaceutical compositions at concentrations of between 0.1 and 20% by weight, and especially between 0.2 and 10% by weight.

The cosmetic compositions are, in particular, intended for use in the form of a lotion, gel, soap, shampoo, aerosol or mousse, and contain at least one compound of formula (I) of one of its salts in a physiologically acceptable vehicle.

The concentration of the compounds of formula (I) in these compositions is preferably between 0.01 and 15% by weight, and especially between 0.05 and 10% by weight.

The compositions according to the invention can contain different additives customary used in cosmetics or in pharmacy, and especially active substances such as hydrating agents, for example thiamorpholine and its derivatives or urea; antiseborrhoeic agents such as S-carboxymethylcysteine, S-benzylcysteamine and their derivatives and thioxolone.

The compounds according to the invention may be combined with compounds which further improve their activity with respect to hair regrowth and/or to checking hair loss, such as, more especially, the following compounds:

nicotinic acid esters including, more especially, $C_1$-$C_6$ alkyl nicotinates, and in particular methyl nicotinate;

steroidal and non-steroidal anti-inflammatory agents well known in the prior art, and especially hydrocortisone, its salts and its derivatives, niflumic acid, and the like;

retinoids, and more especially all-transretinoic acid also known as tretinoin, isotretinoin, retinol and vitamin A and its derivatives, such as the acetate, palmitate or propionate, motretinide, etretinate and zinc all-trans-retinoate;

antibacterial agents selected, more especially, from macrolides, pyranosides and tetracyclines, and in particular erythromycin;

calcium antagonists such as, more especially, cinnarizine and diltiazem;

hormones such as oestriol or analogues or thryoxine and its salts;

anti-androgens such as oxendolone, spironolactone and diethylstilboestrol; and

OH radical trapping agents such as dimethyl sulphoxide.

It is also possible to combine with the compounds of the invention, optionally mixed with the others, compounds such as diazoxide, corresponding to 3-methyl-7-chloro-2H-1,2,4-benzothiadiazine 1,1-dioxide; spiroxasone or 7-(acetylthio)-4',5'-dihydrospiro[androst-4-ene-17,2'-(3'-H)-furan]-3-one; phospholipids such as lecithin; linoleic and lineolenic acids; salicylic acid and its derivatives described in French Patent 2,581,542, and more especially salicylic acid derivatives bearing an alkanoyl group having 2 to 12 carbon atoms at the 5-position of the benzene ring; hydroxy-carboxylic acids and keto-carboxylic acids and their esters and lactones and their corresponding salts; anthralin or 1,8,9-trihydroxyanthracene, carotenoids, and eicosatetraynoic and eicosatriynoic acids, their esters and amides.

The compounds according to the invention may also be combined with surfactant agents including, more especially, those selected from nonionic and amphoteric surfactant agents.

Among nonionic surfactants, there will be mentioned, in particular, the polyhydroxypropyl ethers described in French Patent Nos. 1,477,048, 2,091,516, 2,169,787, 2,328,763 and 2,574,768; oxyethylenated ($C_8$-$C_9$ alkyl) phenols containing from 1 to 100 moles of ethylene oxide, and preferably 5 to 35 moles of ethylene oxide; and alkylpolyglycosides of formula:

$$C_nH_{2n+1}(C_6H_{10}O_5)_xH \qquad (A)$$

in which n varies from 8 to 15 inclusive and x from 1 to 10 inclusive.

Among amphoteric surfactant agents, there will be mentioned, more especially, the amphocarboxyglycinates and amphocarboxypropionates defined in the CTFA Dictionary, 3rd edition, 1982, and sold, in particular, by the company MIRANOL under the name MIRANOL ®.

The compounds according to the invention may be introduced into vehicles which further improve the activity in respect of regrowth, possessing simultaneously advantageous properties from the cosmetic standpoint, such as volatile ternary mixtures of alkylene glycol or dialkylene glycol alkyl ether (preferably $C_1$–$C_4$ alkyl and alkylene), ethyl alcohol and water, the glycol solvent denoting, more especially, ethylene glycol monoethyl ether, propylene glycol monomethyl ether or diethylene glycol monoethyl ether.

The compounds according to the invention may also be introduced into gelled or thickened vehicles, such as essentially aqueous vehicles gelled with heterobiopolysaccharides such as xanthan gum or cellulose derivatives, aqueous-alcoholic vehicles gelled with polyhydroxyethyl acrylate or methacrylate, or essentially aqueous vehicles thickened, especially, with polyacrylic acids crosslinked with a polyfunctional agent, such as the Carbopols sold by the company GOODRICH.

These compositions can also contain preservative agents, stabilizing agents, pH-regulating agents, osmotic pressure-modifying agents, emulsifying agents, UVA and UVB screening agents and antioxidant agents such as α-tocopherol, butylated hydroxyanisole and butylated hydroxytoluene.

The physiologically acceptable medium can consist of water or a mixture of water and a solvent or a mixture of solvents, the solvents being selected from organic solvents acceptable from the cosmetic or pharmaceutical standpoint and selected, more especially, from $C_1$–$C_4$ lower alcohols such as ethyl alcohol, isopropyl alcohol and tert-butyl alcohol, alkylene glycols, and alkylene glycol and dialkylene glycol alkyl ethers such as ethylene glycol monoethyl ether, propylene glycol monomethyl ether and diethylene glycol monoethyl ether. When the solvents are present, they are so in proportions of between 1 and 80% by weight relative to the total weight of the composition.

The physiologically acceptable media may be thickened by means of thickening agents customary used in cosmetics or pharmacy, and heterobiopolysaccharides such as xanthan gum, scleroglucans, cellulose derivatives such as cellulose ethers, and acrylic polymers, cross-linked or otherwise, may be mentioned more especially.

The thickeners are preferably present in proportions of between 0.1 and 5% by weight, and especially between 0.4 and 3% by weight, relative to the total weight of the composition.

The subject of the invention is also a process for cosmetic treatment of the hair or scalp, consisting in applying thereon at least one composition as defined above for the purpose of enhancing the appearance of the hair.

Another subject of the invention consists in the use of the composition defined above for the preparation of a medicinal product having the effect of inducing or stimulating hair growth and checking its loss.

The treatment consists chiefly in applying the composition as defined above on the alopecic areas of an individual's scalp.

The preferred method of application consists in applying 1 to 2 g of the composition on the alopecic area at the rate of one to two applications per day for 1 to 7 days per week over a period of 1 to 6 months.

The compositions can, in particular, be used in the treatment of pelade, hair loss and desquamating dermatitis.

The examples which follow are intended as an illustration of the invention, no limitation of the latter being implied.

PREPARATION EXAMPLE 1

2,4-Diamino-6-(2,2,3,3-tetrafluoropropyloxy)pyrimidine 3-oxide 2 g of sodium are introduced into 100 g of 2,2,3,3-tetrafluoropropanol at 40° C. After the addition of 10 g of 2,4-diamino-6-chloropyrimidine 3-oxide, the reaction mixture is maintained for 32 hours at 90° C.

The reaction mixture is cooled to 0° C. and then filtered to order to remove some insoluble matter. The residue from evaporation of the filtrate to dryness is taken up with 100 cm$^3$ of hexane. Some insoluble matter is removed by filtration. The expected product is obtained after evaporation of the filtrate to dryness. After recrystallization, 11 g of a white powder, melting point 148° C., are obtained.

Elemental analysis for $C_7H_8F_4N_4O_2$

|  | C | H | N | F |
|---|---|---|---|---|
| Calculated | 32.82 | 3.15 | 21.87 | 29.67 |
| Found | 32.65 | 3.24 | 21.80 | 29.60 |

The $^1H$ NMR spectrum is in agreement with the expected structure.

PREPARATION EXAMPLE 2

2,4-Diamino-6-(2-trifluoroethyloxy)pyrimidine 3-oxide 3 g of sodium are introduced into 50 ml of trifluoroethanol at 40° C. After the addition of 10 g of 2,4-diamino-6-chloropyrimidine 3-oxide, the reaction mixture is maintained for 20 hours at 85° C.

The reaction medium is cooled to 0°C. and then filtered in order to remove some insoluble matter. The residue from evaporation of the filtrate to dryness is taken up with dichloromethane and then with hexane in order to remove unreacted trifluoroethanol. The expected product in the form of a white powder is recrystallized in the heated state from acetonitrile. 4.2 g are obtained. It melts at 205° C.

Elemental analysis for $C_6H_7F_3N_4O_2$

|  | C | H | N | F |
|---|---|---|---|---|
| Calculated | 32.15 | 3.15 | 25.00 | 25.43 |
| Found | 31.63 | 2.97 | 24.67 | 25.08 |

The $^1H$ NMR spectrum is in agreement with the expected structure.

PREPARATION EXAMPLE 3

2,4-Diacetamido-6-(2',2',2'-trifluoroethoxy)-N-pyrimidine 3-oxide 90 ml of dichloromethane, 11.1 g triethylamine and 6 g 2,4-diamino-6-(2',2',2'-trifluoroethoxy)-N-pyrimidine 3-oxide are placed in a 250-ml three-necked flask saturated with an argon atmosphere. 8.65 g of acetyl chloride are added dropwise to the mixture which is cooled to between 0° and 5° C.

After a reaction time of 8 hours 30 min, the reaction mixture is washed with:

2×40 ml of water
60 ml of a 1% Na₂CO₃ solution
2×40 ml of water.

The organic phase is dried over Na₂SO₄. After filtering off the Na₂SO₄, the filtrate is concentrated to one third of the solvent. The product is precipitated by the addition of 250 ml hexane. This product is recrystallized from a ½ hexane/acetone mixture.

2.25 g of 2,4-diacetamido-6-(2',2',2'-trifluoroethoxy)-N-pyrimdine 3-oxide are obtained. (Yld=27%). b.p.=183°–185° C.

Elemental analysis: $C_{10}H_{11}F_3N_4O_4$ M=308.2 g

|  | C | H | N | F |
|---|---|---|---|---|
| Calculated | 38.97 | 3.60 | 18.18 | 18.49 |
| Found | 39.55 | 3.66 | 18.11 | 18.05 |

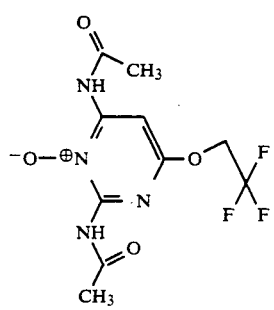

The mass and ¹HNMR spectra are in agreement with the expected structure.

PREPARATION EXAMPLE 4

2,4-Dimethoxycarbonylamino-6-(2',2', 2'-trifluoroethoxy)-N-pyrimidine 3-oxide 60 ml of dichloromethane, 16.7 g of triethylamine and 6 g of 2,4-diamino-6-(2', 2', 2'-trifluoroethoxy)-N-pyrimidine 3-oxide are placed in a 250-ml three-necked flask saturated with an argon atmosphere. 15.6 g of methyl chloroformate are added dropwise to this mixture at between 0° and 5° C.

After stirring for 16 hours at ambient temperature, the reaction mixture is washed with:

4×20 ml of a 1% HCl solution
3×20 ml of water (to neutrality of the aqueous phase).

The organic phase is dried over Na₂SO₄ and the solvent is evaporated under vacuum. The crude product collected is taken up in 50 ml of ethyl ether and filtered. After evaporation of the filtrate, a viscous liquid is obtained which is brought to reflux in 80 ml of methanol. A precipitate forms, which is filtered hot and dried under vacuum and over P₂O₅ for 12 hours.

5.4 g of 2,4-dimethoxycarbonylamino-6-(2',2',2'-trifluoroethoxy)-N-pyrimidine 3-oxide are thus recovered. (Yld=59%). b.p.=184°–185° C.

Elemental analysis: $C_{10}H_{11}F_3N_4O_5$ M-340.2 g

|  | C | H | N | F |
|---|---|---|---|---|
| Calculated | 35.30 | 3.26 | 16.47 | 16.75 |
| Found | 35.36 | 3.21 | 16.27 | 16.78 |

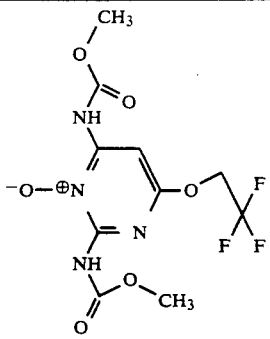

The mass and ¹H NMR spectra are in agreement with the expected structure.

COMPOSITION EXAMPLE 1

The following composition is prepared:

| 2,4-Diamino-6-(2,2,3,3-tetrafluoropropyloxy)pyrimidine 3-oxide | 6.0 g |
|---|---|
| Absolute ethanol/propylene glycol mixture (95:5) qs | 100.0 g |

COMPOSITION EXAMPLE 2

The following composition is prepared:

| 2,4-Diamino-6-(2-trifluoroethyloxy)-pyrimidine 3-oxide | 10.0 g |
|---|---|
| Propylene glycol | 20.0 g |
| Ethanol | 50.0 g |
| Water qs | 100.0 g |

These two compositions are presented in the form of a lotion.

1 to 2 g of this composition is/are applied on the alopecic areas of the scalp, optionally accompanied by a massage to promote penetration, at the rate of one to two applications per day during 3 months of treatment.

A similar composition in the form of a lotion is prepared by replacing the pyrimidine 3-oxide derivative by respectively those of Preparation Examples 3 and 4.

We claim:

1. Composition intended for use in topical application, comprising, in a physiologically acceptable medium, at least a compound corresponding to the formula:

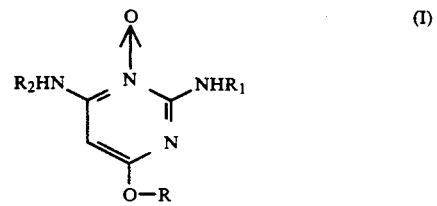

in which:

R₁ and R₂ denote, independently of one another, a hydrogen atom or a carbamoyl of formula:

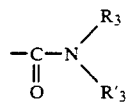

(B)

in which R'$_3$ denotes hydrogen or R$_3$; an alkoxy-carbonyl group of formula:

(C)

or an acyl group of formula:

(D)

in which R$_3$ denotes a linear or branched C$_1$-C$_{18}$ alkyl radical, a C$_2$-C$_{18}$ alkenyl group, a C$_5$-C$_8$ cycloalkyl group or an aryl or aralkyl radical corresponding to the formula:

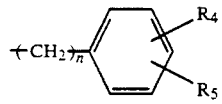

(E)

in which:

n is 0 to 4;

R$_4$ and/or R$_5$, independently of one another, denote hydrogen, a C$_1$-C$_6$ lower alkyl group, a hydroxyl or alkoxy group or a halogen atom, at least one of the radicals R$_1$ or R$_2$ being other than hydrogen; and R denotes a linear or branched C$_1$-C$_6$ alkyl radical substituted with one or more halogen atoms.

2. Composition intended for use in cosmetics, in the form of a lotion gel, soap, shampoo, aerosol or mousse, comprising a cosmetically acceptable vehicle and, in a concentration of between 0.01 and 15% by weight, at least one compound corresponding to the formula:

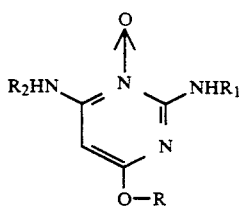

(I)

in which:

R$_1$ and R$_2$ denote, independently of one another, a hydrogen atom or a carbamoyl group of formula:

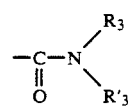

(B)

in which R'$_3$ denotes hydrogen or R$_3$; an alkoxy-carbonyl group of formula:

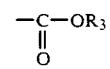

(C)

or an acyl group of formula:

(D)

in which R$_3$ denotes a linear or branched C$_1$-C$_{18}$ alkyl radical, a C$_2$-C$_{18}$ alkenyl group, a C$_5$-C$_8$ cycloalkyl group or an aryl or aralkyl radical corresponding to the formula:

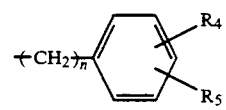

(E)

in which:

n is 0 to 4;

R$_4$ and R$_5$, independently of one another, denote hydrogen, a C$_1$-C$_6$ lower alkyl group, a hydroxyl or alkoxy group or a halogen atom, at least one of the radicals R$_1$ or R$_2$ being other than hydrogen; and R denotes a linear or branched C$_1$-C$_6$ alkyl radical substituted with one or more halogen atoms.

3. Composition according to claim 1, in the form of an ointment, tincture, cream, pomade, powder, patch, impregnated pad, solution, emulsion, vesicular emulsion, lotion, gel, spray or anhydrous or aqueous suspension, for the purpose of its pharmaceutical application, and containing at least a compound of formula (I) as defined in claim 1.

4. Composition according to claim 1, wherein the compound(s) of formula (I) is (are) present at concentrations of between 0.1 and 20% by weight relative to the total weight of the composition.

5. Composition according to claim 1, containing, in addition, hydrating agents, antiseborrhoeic agents.

6. Composition according to claim 1, containing, in additional agents, improving the activity in respect of hair regrowth and/or of retarding hair loss.

7. Composition according to claim 6, containing additional agents improving the activity of hair regrowth and/or of retarding hair loss, which are nicotinic acid esters, steroidal or non-steroidal anti-inflammatory agents, retionids, antibacterial agents, calcium antagonists, hormones, anti-androgens, OH radical trapping agents or their mixtures.

8. Composition according to claim 6, containing additional compounds improving the activity with respect to hair regrowth and/or retarding hair loss, selected from diazoxide, spiroxasone, phospholipids, linoleic and linoleic acids, salicyclic acid and its derivatives, hydroxy-carboxylic or keto-carboxylic acids, their esters and lactones and their corresponding salts, anthralin or 1,8,9-trihydroxyanthracene, carotenoids, and 5,8,11,14-eicosatetraynoic and 5,8,11-eicosatriynoic acids, their esters and amides.

9. Composition according to claim 1, wherein the physiologically acceptable medium consists of water or a mixture of water and one or more organic solvent(s), or of a mixture of organic solvents, the organic solvents being pharmaceutically or cosmetically acceptable.

10. Composition according to claim 9, wherein the solvents are selected from $C_1$–$C_4$ lower alcohols, alkylene glycols, and mono- and dialkylene glycol alkyl esters.

11. Composition according to claim 1, wherein the physiologically acceptable medium is thickened by means of thickening and/or gelling agents, and contains preservative agents, stabilizing agents, pH-regulating agents, osmotic pressure-modifying agents, emulsifying agents, UVA and UVB screening agents antioxidant agents.

12. Composition according to claim 1, further containing surfactant agents selected from nonionic and amphoteric surfactant agents.

13. A process for cosmetic treatment of hair or scalp, characterized in that an effective amount of the composition as defined in claim 1 is applied to the hair or scalp.

14. Method of use of the composition as defined in claim 1 in the therapeutic treatment of hair loss, comprising applying an effective amount of said composition to the hair or the scalp.

* * * * *